United States Patent
Randolph

(10) Patent No.: US 8,603,013 B2
(45) Date of Patent: Dec. 10, 2013

(54) PRESSURE SWITCHES, TRANSMITTERS, SYSTEMS, AND METHODS FOR MONITORING A PRESSURE AT A TISSUE SITE

(75) Inventor: Larry Tab Randolph, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 406 days.

(21) Appl. No.: 12/404,067

(22) Filed: Mar. 13, 2009

(65) Prior Publication Data

US 2009/0234249 A1 Sep. 17, 2009

Related U.S. Application Data

(60) Provisional application No. 61/036,433, filed on Mar. 13, 2008.

(51) Int. Cl.
*A61B 5/11* (2006.01)

(52) U.S. Cl.
USPC .......................................... 600/592; 600/587

(58) Field of Classification Search
USPC ................................................ 600/587, 592
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Guiles, Jr. | |
| 3,568,675 A | 3/1971 | Harvey | |
| 3,648,692 A | 3/1972 | Wheeler | |
| 3,682,180 A | 8/1972 | McFarlane | |

(Continued)

FOREIGN PATENT DOCUMENTS

| JP | H-9054 | 2/1992 |
|---|---|---|
| KR | 10-2002-0048890 A | 6/2002 |

(Continued)

OTHER PUBLICATIONS

Full International Search Report and Written Opinion date mailed Dec. 21, 2009; PCT International Application No. PCT/US2009/037153.

(Continued)

*Primary Examiner* — Sean Dougherty

(57) ABSTRACT

Apparatuses, systems, and methods for monitoring a pressure exerted on a tissue site are provided. In one embodiment, an apparatus includes a pressure switch adapted for placement adjacent the tissue site. The pressure switch includes an antenna operable to receive a first signal, a diode disposed adjacent the antenna, and a membrane covering the antenna and the diode. The membrane is movable from an unpressed position to a pressed position when a force is exerted on the membrane to cause electrical communication between the antenna and the diode. The antenna is operable to send a second signal when the membrane is in the pressed position. The apparatus may also include a transmitter operable to emit the first signal to the antenna. The transmitter may output an alert when the transmitter receives the second signal.

19 Claims, 4 Drawing Sheets

(56) References Cited

U.S. PATENT DOCUMENTS

| | | |
|---|---|---|
| 3,826,254 A | 7/1974 | Mellor |
| 4,074,227 A | 2/1978 | Kalmus |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,541,574 A | 7/1996 | Lowe |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,642,096 A | 6/1997 | Leyerer et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,273,863 B1 | 8/2001 | Avni et al. |
| 6,287,253 B1 * | 9/2001 | Ortega et al. ............... 600/300 |
| 6,287,316 B1 | 9/2001 | Agarwal et al. |
| 6,345,623 B1 | 2/2002 | Heaton et al. |
| 6,409,674 B1 | 6/2002 | Brockway et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,855,115 B2 | 2/2005 | Fonseca et al. |
| 7,059,195 B1 | 6/2006 | Liu et al. |
| 7,355,519 B2 * | 4/2008 | Grold et al. ............... 340/573.7 |
| 7,878,055 B2 * | 2/2011 | Balzano ..................... 73/172 |
| 2002/0049394 A1 | 4/2002 | Roy et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0064037 A1 | 3/2006 | Shalon et al. |

FOREIGN PATENT DOCUMENTS

| | | |
|---|---|---|
| KR | 20-2007-0000487 U | 4/2007 |
| WO | WO 98/25552 A1 | 6/1998 |
| WO | WO 01/00089 A | 1/2001 |
| WO | WO 02/098271 A | 12/2002 |
| WO | WO 2005/094679 A1 | 10/2005 |
| WO | WO 2008/003920 A | 1/2008 |

OTHER PUBLICATIONS

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

Va. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

International Partial Search Report issued Jul. 22, 2009 for International PCT Application No. PCT/US2009/037153.

* cited by examiner

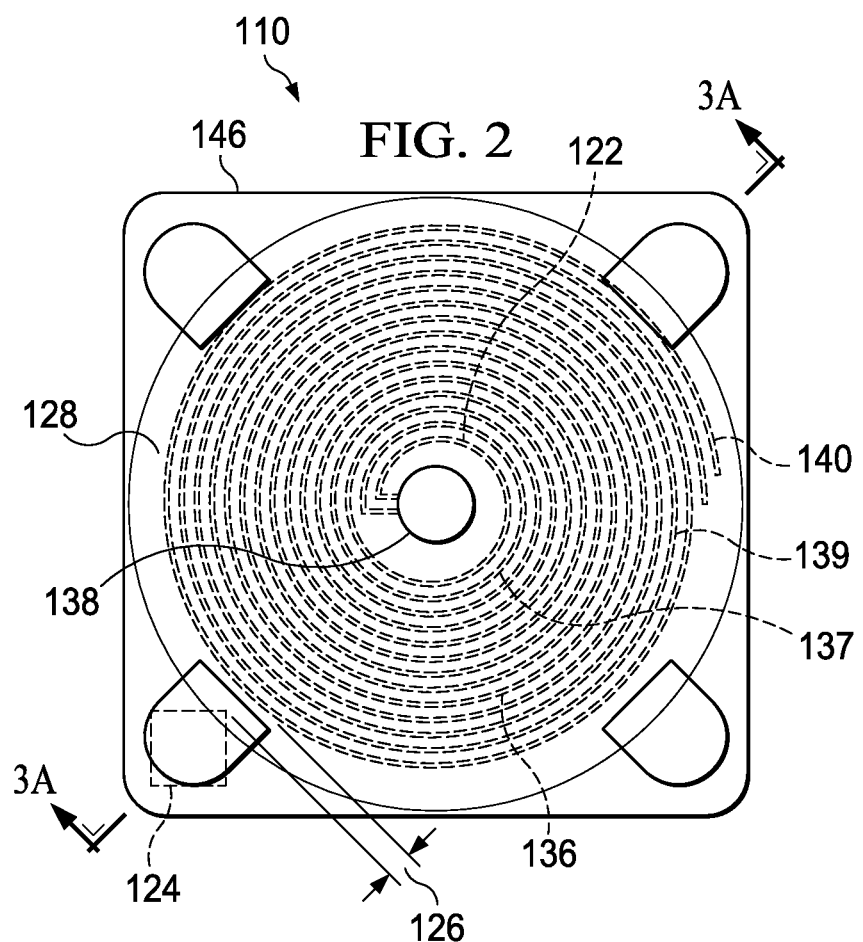

PRESSURE SWITCHES, TRANSMITTERS, SYSTEMS, AND METHODS FOR MONITORING A PRESSURE AT A TISSUE SITE

CROSS-REFERENCE TO RELATED APPLICATIONS

This application claims the benefit of U.S. Provisional Application No. 61/036,433 filed Mar. 13, 2008, which is hereby incorporated by reference.

BACKGROUND

The illustrative embodiments relate generally to medical treatment systems and, more particularly, to pressure switches, transmitters, systems, and methods for monitoring a pressure at a tissue site.

Tissue sites on a patient's body often experience varying levels of pressure due to the position or behavior of the patient. A patient or caretaker may desire to know whether the pressure exerted on a particular tissue site is excessive. By way of example, the foot ulcers experienced by a diabetic patient may undergo varying levels of pressure due to certain behaviors, such as walking. Off-loading shoes or boots may be used to alleviate pressure on the foot ulcer, but do not always effectively reduce the pressure on the foot ulcers. In addition, more than 82 percent of diabetic patients may also lack the protective sensation to determine whether excessive amounts of pressure are being exerted on the ulcer. This lack of protective sensation may be caused by peripheral neuropathy, which often afflicts diabetic patients having ulcers.

SUMMARY

According to an illustrative embodiment, an apparatus for monitoring a pressure exerted on a tissue site includes a pressure switch adapted for placement adjacent the tissue site. The pressure switch includes an antenna operable to receive a first signal, a diode disposed adjacent the antenna, and a membrane covering the antenna and the diode. The membrane is movable from an unpressed position to a pressed position when a force is exerted on the membrane to cause electrical communication between the antenna and the diode. The antenna is operable to send a second signal when the membrane is in the pressed position. The apparatus may also include a transmitter operable to emit the first signal to the antenna. The transmitter may output an alert when the transmitter receives the second signal.

In another embodiment, a method for monitoring a pressure exerted on a tissue site includes receiving a first signal from a transmitter, detecting a force at the tissue site, and sending a second signal to the transmitter in response to detecting the force.

In another embodiment, a method for monitoring a pressure exerted on a tissue site includes sending a first signal from a transmitter, and outputting an alert in response to receiving a second signal from a pressure switch adjacent the tissue site.

Other objects, features, and advantages of the illustrative embodiments will become apparent with reference to the drawings and detailed description that follow.

BRIEF DESCRIPTION OF THE DRAWINGS

FIG. 2 illustrates a top view of a pressure switch of the system of FIGS. 1A and 1B according to an illustrative embodiment;

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figures 1A, 1B:
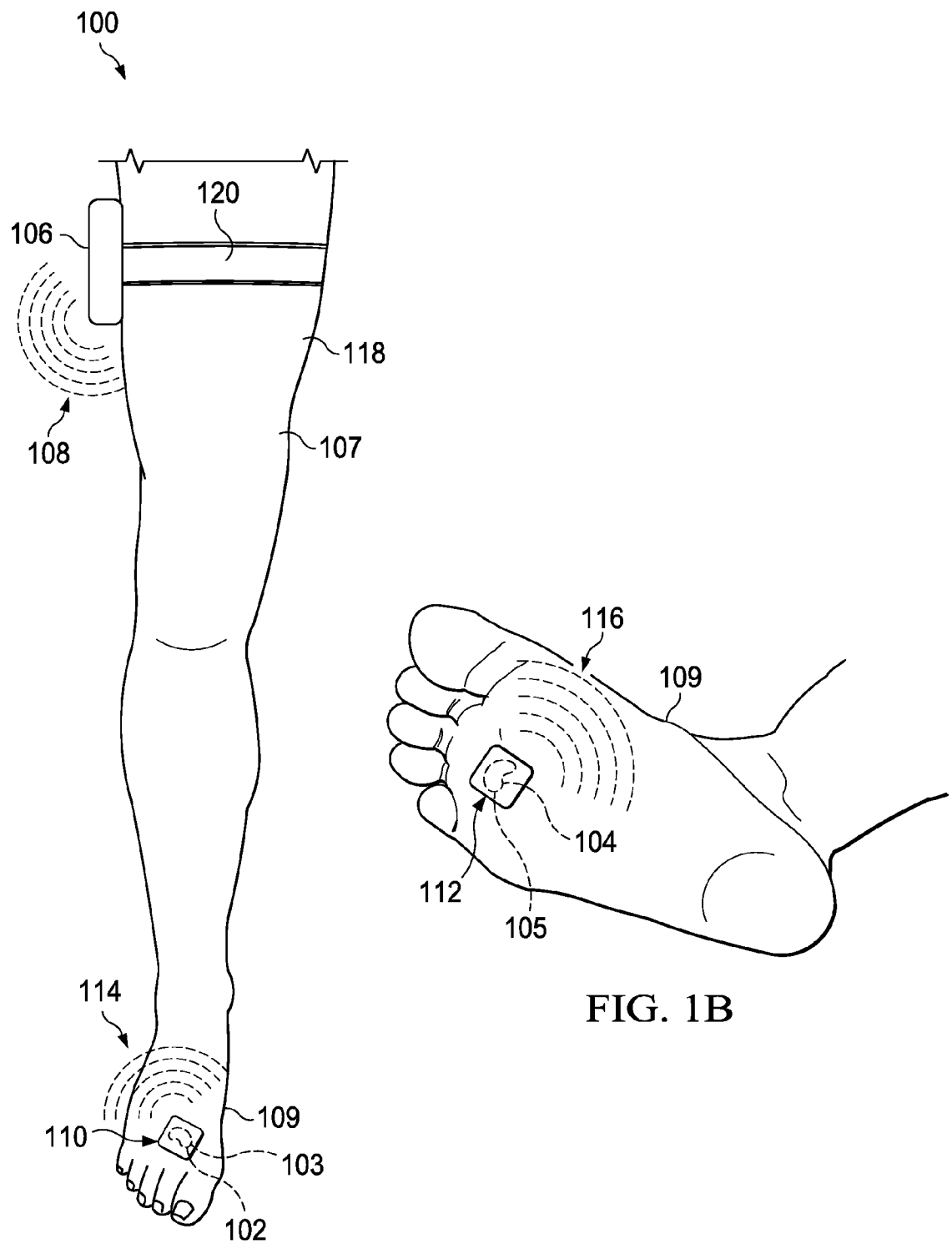
FIG. 1A illustrates a front view of a system for indicating a pressure exerted on a tissue site according to an illustrative embodiment.
FIG. 1B illustrates a bottom view of the foot shown in FIG. 1A.

Referring to FIGS. 1A and 1B, a system 100 for indicating a pressure exerted on a tissue site according to an illustrative embodiment includes a transmitter 106 and at least one pressure switch 110. In the embodiment illustrated in FIGS. 1A and 1B, two tissue sites 102, 104 are located on a foot of a patient 107. Pressure switch 110 is positioned at the tissue site 102, and a second pressure switch 112 is positioned at the tissue site 104. In system 100, the transmitter 106 is worn by the patient 107 and emits a first signal 108. The pressure switches 110, 112 receive the first signal 108 from the transmitter 106. Each of the pressure switches 110, 112 is capable of detecting the pressure exerted on the tissue sites 102, 104. The pressure switch 110 may emit a second signal 114 when the pressure exerted on the tissue site 102 exceeds an amount that changes the state of the pressure switch 110. Similarly, the pressure switch 112 may emit a second signal 116 when the pressure exerted the tissue site 104 exceeds a amount that changes the state of the pressure switch 112. Upon receiving either or both of the second signals 114, 116, the transmitter 106 may alert the patient 107 in a variety of ways, such as by vibrating or emitting an audio or visual alert. The first and second signals 108, 114, 116 may be any wireless signal, including, without limitation, electromagnetic, radio, or Bluetooth signals.

The tissue sites 102 and 104, in the example of FIGS. 1A and 1B, are foot ulcers 103, 105. The alert emitted by transmitter 106 in response to pressure at the foot ulcers 103, 105 may alert the patient 107 when there is excessive pressure on the foot ulcers 103, 105. Such an alert may be used when the patient 107 may be otherwise unable to properly determine the pressure being exerted on the foot ulcers 103, 105, such as when the patient 107 suffers from peripheral neuropathy. By alerting the patient 107 when excessive pressure is being applied to the foot ulcers 103, 105, the patient 107 may take measures to alleviate the pressure on the foot ulcers 103, 105, such as by altering the patient's position, weight distribution, or movement. Thus, aggravation or worsening of the foot ulcers 103, 105 may be prevented.

While the pressure switches 110, 112 have been described as being used with foot ulcers 103, 105, the pressure switches 110, 112 may instead be placed on or adjacent to any part of the patient's 107 body, including those parts where ulcers or other wounds may be subjected to prolonged pressure. For example, the pressure switches 110, 112 may be placed on or adjacent the patient's 107 heel, shoulder blades, or buttocks.

In addition, any number of pressure switches 110, 112 may be placed on the patient's 107 body, depending upon the number of tissue sites to be monitored by the system 100. In one embodiment, when more than one pressure switch is placed on the patient's 107 body, the transmitter 106 may output a different alert depending on the pressure switch from which the second signal is received. For example, the transmitter may output a different audio alert depending on whether the transmitter 106 receives the second signal 114 from the pressure switch 110 or the second signal 116 from the pressure switch 112.

The pressure switches 110, 112 may be placed adjacent the tissues sites 102 and 104 by adhering the pressure switches 110, 112 to locations other than the tissue sites 102, 104 themselves. The pressure switches 110, 112 may be adhered, or otherwise placed, on an article of clothes worn by the patient 107, including, without limitation, a shoe, off-loading boot/shoe, shirt, or sock, such that the pressure switches 110, 112 are adjacent the tissue sites 102, 104 when the article is worn. For example, the pressure switches 110, 112 may be adhered to an insole, or inner surface, of an off-loading boot intended to alleviate pressure from the foot ulcers 103, 105 such that the pressure switches 110, 112 are adjacent the foot ulcers 103, 105 when the boot is worn by the patient 107.

In one embodiment, the transmitter 106 is secured to the patient's leg 118 by a strap 120. In other embodiments, the transmitter 106 may be secured to any part of the patient's 107 body, an article being worn by the patient 107, or coupled to one or more of the pressure switches 110, 112. Also, in lieu of or addition to the strap 120, the transmitter 106 may use any attachment mechanism to directly or indirectly attach to the patient's 107 body, such as a buckle, velcro, a magnet, a hook, a harness, or any other attachment device. In another embodiment, the transmitter 106 may not be secured to the patient's 107 body, but instead held or placed in an article worn by the patient 107, such as a pocket or purse. The location and attachment mechanism used by the transmitter 106 may depend on the output that is emitted by the transmitter 106 when the second signals 114, 116 are received. For example, if the transmitter 106 emits an audio, visual, or vibrational output, the transmitter 106 may be located where the transmitter 106 may be heard, seen, or felt by the patient 107, respectively.

In another embodiment, a tactile feedback device (not shown) may be coupled to, adjacent, or inside one or both of the pressure switches 110, 112. In one example, the pressure switches 110, 112 and one or more tactile feedback devices may be located inside of an article of footwear, such as an off-loading boot. When either or both of the pressure switches 110, 112 detect a force, the tactile feedback device may output a tactile alert to the patient 107. The tactile alert may include vibration, including one or more taps, or electrical stimulation.

Figure 3A:
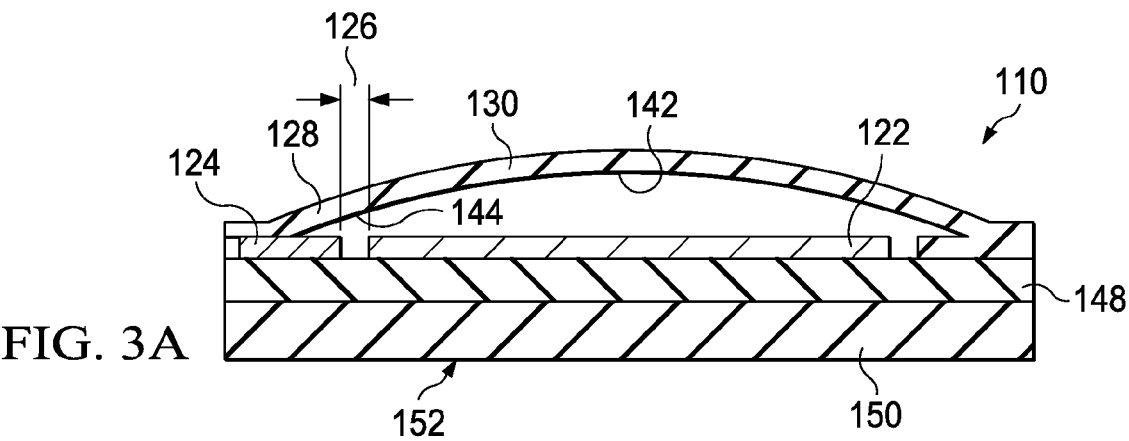
FIG. 3A illustrates a cross-sectional side view of the pressure switch of FIG. 2 taken along line 3A-3A.
Figure 3B:
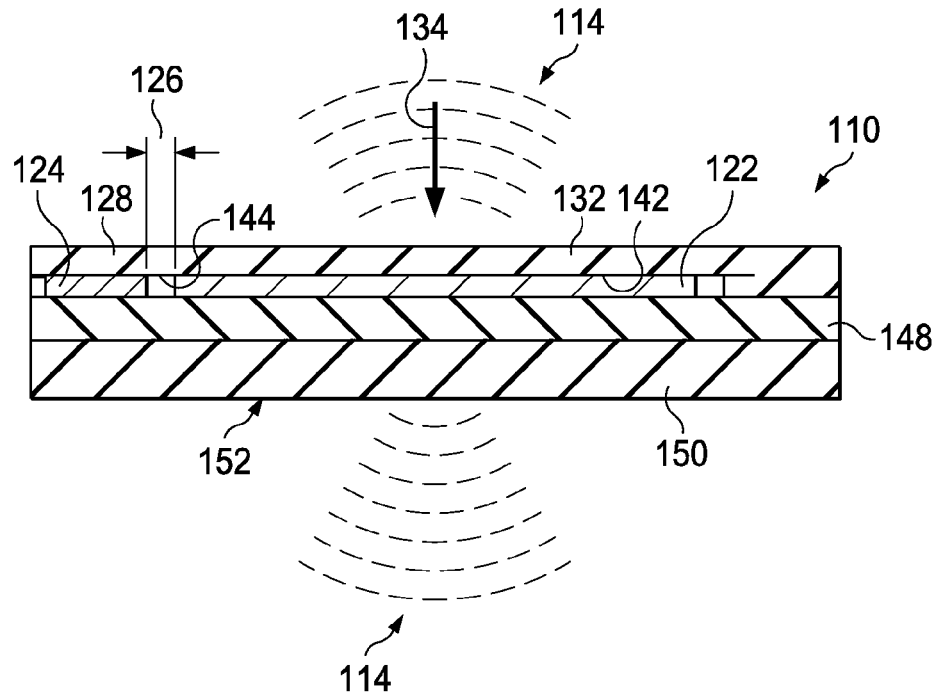
FIG. 3B illustrates a cross-sectional side view of the pressure switch of FIG. 3A, the pressure switch being shown in a pressed position.

Referring to FIGS. 2, 3A, and 3B, the pressure switch 110 includes an antenna 122 and a diode 124 that is separated from the antenna 122 by a gap 126. The pressure switch 110 also includes a membrane 128 that is movable between an unpressed position 130 and a pressed position 132 based on a force 134 exerted on the membrane 128. When the force 134, which may be a pressure, is exerted on the membrane 128, the membrane 128 moves from the unpressed position 130 to the pressed position 132 to cause electrical communication between the antenna 122 and the diode 124. The electrical communication between the antenna 122 and the diode 124 causes the antenna 122 to emit the second signal 114, which may be received by the transmitter 106 and cause the transmitter 106 to output an alert. Thus, a patient may be alerted when the pressure or force on a tissue site collapses the membrane 128 into the pressed position.

The antenna 122 may be formed from a conducting conduit 136. The conducting conduit 136 may be made from any conducting material, such as metal. In one embodiment, the metal used to form the conducting conduit 136 may be stainless steel or any resilient material that is capable of returning to an original shape after the force 134 is removed. The conducting conduit 136 may also form a spiral, such as that shown in FIG. 2. An inner portion 137 of the spiral may terminate at about the center 138 of the pressure switch 110, and an outer portion 139 of the spiral may terminate at a periphery 140 of the pressure switch 110. In one embodiment, the outer portion 139 may terminate just before reaching the diode 124 to form the gap 126.

The pressure switch 110 may be a passive device that does not require an independent power source, such as a battery. In one embodiment, the first signal 108 from the transmitter 106 may cause the diode 124 to agitate or have a current. In the pressed position 132, the membrane 128 may directly or indirectly touch both the antenna 122 and the diode 124 to electrically bridge the gap 126, or close the circuit, between the antenna 122 and the diode 124. In this manner, any agitation or current from the diode 124 is communicated to the antenna 122, thereby causing the antenna 122 to emit the second signal 114.

The material from which the membrane 128 is formed may facilitate electrical communication between the antenna 122 and the diode 124 when the membrane 128 touches both the antenna 122 and the diode 124. In one embodiment, the membrane 128 may be formed from a conducting material, such as metal. In another embodiment, an inner surface 142 of the membrane 128 may be coated, or otherwise include, a conducting material. In yet another embodiment, only a portion 144 of the inner surface 142 of the membrane 128 may be coated, or otherwise include, a conducting material.

Although the membrane 128 is shown to form a dome shape, the membrane 128 may have any shape that allows the membrane 128 to have unpressed and pressed positions. For example, the membrane 128 may be a button that, when pressed, causes electrical communication between the antenna 122 and the diode 124 by electrically bridging the gap 126. The pressure switch 110 also has a low-profile, which may allow the pressure switch 110 to be unobtrusively placed adjacent a tissue site or hide the pressure switch 110 when located under an article of clothes worn by a patient. For example, the low-profile of the pressure switch 110 facilitates the placement of the pressure switch 110 on a patient's foot while the patient wears a shoe or off-loading boot, and may help to reduce discomfort experienced by the patient.

In addition, although the perimeter 146 of the pressure switch 110 has an approximately square shape, the perimeter 146 may have any shape, such as a circular, elliptical, rectangular, polygonal, or customized shape. In the embodiment in which the perimeter 146 of the pressure switch 110 is a customized shape, a user may cut, or otherwise shape, the pressure switch 110 to adapt to the tissue site or other object adjacent to which the pressure switch 110 will be applied.

The amount of force 134 required to move the membrane 128 from the unpressed position 130 to the pressed position 132 may depend on a variety of factors. Such factors may include, without limitation, the shape of the membrane 128, the thickness of the membrane 128, the material from which the membrane 128 is formed, the curvature of the membrane 128, and the conductivity of the membrane 128. One may desire to adjust the amount of force 134 that is required to move the membrane 128 from the unpressed position 130 to the pressed position 132 for a variety of reasons. For example, the force 134 may be varied based on the location of the tissue site adjacent to which the pressure switch 110 is to be placed to take account of the varying amounts of pressure normally experienced by different parts of the body.

When all or a portion of the force 134 is removed from the membrane 128, the membrane 128 may move from the pressed position 132 to the unpressed position 130, including any position intermediate between the pressed position 132 and the unpressed position 130. In the unpressed position 130, the membrane 128 does not electrically bridge the gap 126 between the antenna 122 and the diode 124. Little or no electrical communication may occur across the gap 126 when the membrane 128 is in the unpressed position 130.

Referring now specifically to FIGS. 3A and 3B, the pressure switch 110 may include a padding layer 148. The antenna 122 and the diode 124 are disposed between the padding layer 148 and at least a portion of the membrane 128. The pressure switch 110 may also include an adhesive layer 150 that is adapted to adhere the pressure switch 110 adjacent or onto a tissue site. The adhesive layer 150 is located on a contacting side 152 of the pressure switch 110, which may adhere, or otherwise contact, a tissue site or an object adjacent or near the tissue site. Also, the padding layer 148, the antenna 122, or the diode 124 may be disposed between the adhesive layer 150 and at least a portion of the membrane 128.

The padding layer 148 may buffer, or otherwise provide separation, between the antenna 122, diode 124, or membrane 128, and the surface onto which the pressure switch 110 is adhered. By way of example, the padding layer 148 may prevent the antenna 122 and the diode 124, which may be formed from metal, from irritating or touching a tissue site to which the pressure switch 110 may be adhered. The padding layer 148 may be composed of any cushioning or shock-absorbing material, such as a gel. In one embodiment, the padding layer 148 may have adhesive characteristics such that the padding layer 148 may incorporate the function of the adhesive layer 150, dispensing with the need to include a separate adhesive layer 150.

The force 134 that causes the membrane 128 to move from the unpressed position 130 to the pressed position 132 may be from any source, such as those described with respect to FIGS. 1A and 1B. In the example in which the contacting side 152 of membrane 128 contacts a tissue site, the force 134 may be from contact with an object that is pressed against the tissue site as a result of the position or movement of the patient. For example, a floor or shoe may press against the membrane 128 as a result of walking when the pressure switch 110 is adhered to a plantar region of the patient's foot. In the example in which the contacting side 152 of the membrane 128 contacts an object, such as an article of clothes, adjacent the tissue site, the force 134 may originate from contact with the tissue site itself. For example, if the pressure switch 110 is adhered to the insole of a shoe, the plantar portion of a patient's foot may directly or indirectly press against the membrane 128 as the patient walks.

In one embodiment, while the pressure switch 110 is receiving a first signal, such as the first signal 108 in FIGS. 1A and 1B, from a transmitter, the membrane 128 may collapse into the pressed position 132 due to the force 134 on the membrane 128, and cause electrical communication between the antenna 122 and the diode 124. The antenna 122 may emit the second signal 114 in response to this electrical communication between the antenna 122 and the diode 124. The second signal 114 may be received by the transmitter.

Figure 4:
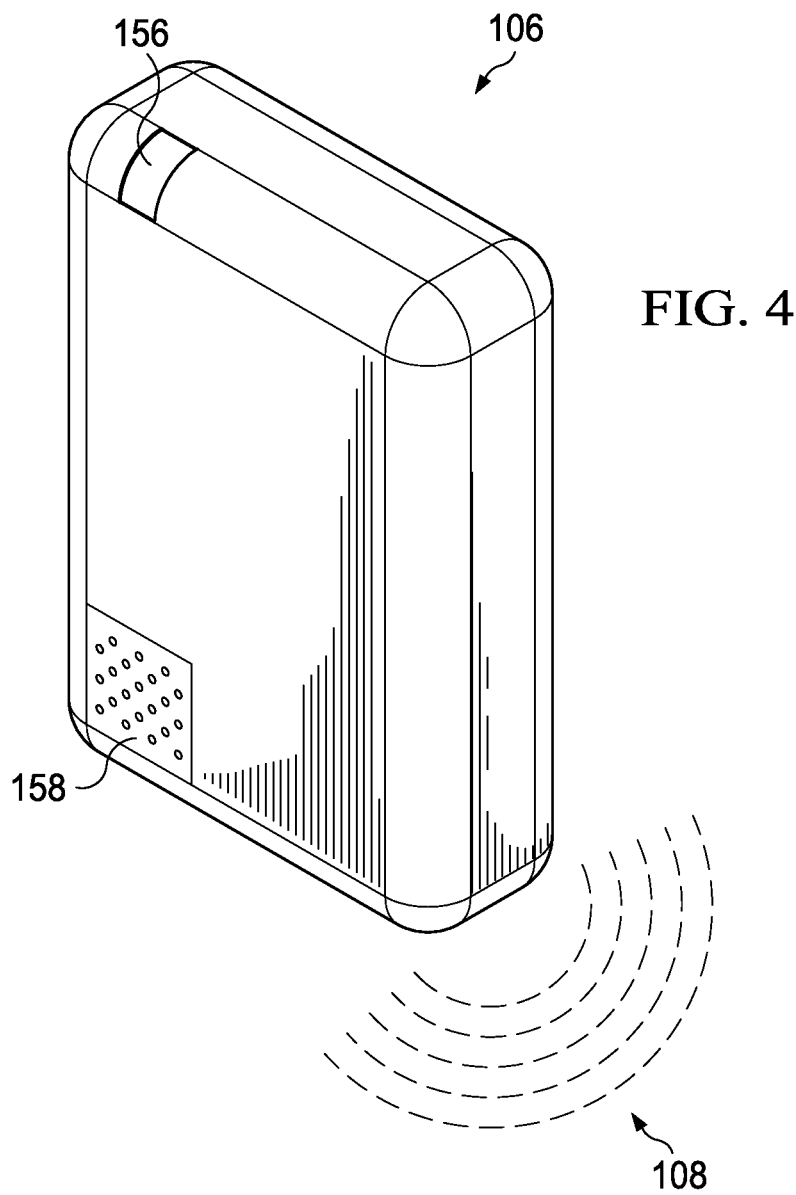
FIG. 4 illustrates a perspective view of a transmitter of the system of FIG. 1A according to an illustrative embodiment.

Referring to FIG. 4, the transmitter 106 is shown according to an illustrative embodiment. The transmitter 106 outputs an alert to a patient upon receiving a second signal from a pressure switch, such as the second signals 114, 116 in FIGS. 1 and 3B, thereby alerting a patient that pressure is being exerted on the tissue site adjacent the pressure switch. The first signal 108 emitted by the transmitter 106 may serve as the power source that powers the pressure switches, which may be passive. The power derived from the first signal 108 may allow the pressure switches to transmit signals back to the transmitter 106. In addition, the transmitter 106 may continuously or intermittently emit the first signal 108.

The transmitter 106 may include one or more output devices that allow the transmitter 106 to output an alert when a signal is received from a pressure switch. For example, the transmitter 106 may include a vibrational device (not shown) located inside the transmitter 106 that causes the transmitter 106 to vibrate. Thus, a patient feeling the vibration of the transmitter 106 may be alerted to the presence of excess pressure at a tissue site. The transmitter 106 may also include a light emitting device 156 that emits light to visually alert a patient when a signal is received from a pressure switch. The transmitter 106 may also include a speaker 158 that emits a sound to audibly alert a patient when a signal is received from a pressure switch. The transmitter 106 may also have an electrical output device (not shown) that electrically stimulates a patient when a signal is received from a pressure switch. Other types of output devices may also be included with the transmitter 106.

The transmitter 106 may also have any shape or size. For example, one or more surfaces of the transmitter 106 may be curved to contour a patient's body, such as when the transmitter 106 is worn on the body of the patient. In another example, the transmitter 106 may be small in size to permit convenient and unobtrusive carrying of the transmitter 106 by the patient.

In an alternate embodiment, the transmitter 106 may output an alert only when the transmitter 106 receives a signal from a pressure switch for a predetermined period of time, such as one second, five seconds, or ten seconds. In this embodiment, the patient would not be alerted by the transmitter 106 when the pressure exerted on the pressure switch is only insignificant, momentary, or for a very short period of time.

Although the illustrative embodiments described herein have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

What is claimed is:

1. A system for monitoring a pressure exerted on a tissue site, the system comprising:
    a transmitter operable to propagate a first signal, the first signal being a radio frequency signal, and emitting an alert when the transmitter receives a second signal in response to the first signal; and
    a pressure switch adapted for placement adjacent the tissue site and to be responsive to a force applied at the tissue site, the pressure switch comprising:

an antenna operable to receive the first signal and propagate the second signal;

a diode disposed adjacent the antenna and electrically connected to the antenna to rectify the second signal;

a switch electrically connected to the antenna and the diode for completing a circuit when closed; and a membrane covering the antenna and the diode, the membrane movable from an unpressed position to a pressed position when the force is exerted on the membrane to close the switch;

whereby the antenna propagates the second signal when the membrane is in the pressed position.

2. The system of claim 1, wherein the transmitter vibrates when the transmitter receives the second signal.

3. The system of claim 1, wherein the antenna is formed from a conducting conduit, and wherein the conducting conduit forms a spiral.

4. The system of claim 1, wherein the switch comprises a gap between the antenna and the diode, and a conductive material on an antenna-facing side of the membrane to electrically close the gap when the membrane is in the pressed position.

5. The system of claim 1, wherein the membrane moves from the pressed position to the unpressed position when at least a portion of the force is removed from the membrane.

6. The system of claim 1, wherein the membrane is shaped to form a dome.

7. The system of claim 1, wherein the pressure switch is a passive device.

8. The system of claim 1, wherein the pressure switch further comprises:

an adhesive layer adapted to adhere the pressure switch adjacent the tissue site, and wherein the antenna is disposed between the adhesive layer and the membrane.

9. The system of claim 1, wherein the pressure switch further comprises:

an adhesive layer adapted to adhere the pressure switch to the tissue site, and wherein the antenna is disposed between the adhesive layer and the membrane.

10. The system of claim 1, wherein the pressure switch further comprises:

a padding layer, and wherein the antenna and the diode are disposed between the padding layer and the membrane.

11. The system of claim 1, wherein the pressure switch further comprises:

a padding layer formed from a gel, and wherein the antenna and the diode are disposed between the padding layer and the membrane.

12. The system of claim 1, wherein the pressure switch further comprises:

an adhesive layer adapted to adhere the pressure switch adjacent the tissue site, wherein the antenna is disposed between the adhesive layer and the membrane; and a padding layer disposed between the adhesive layer and the antenna.

13. The system of claim 1, wherein:

the antenna is formed from a conducting conduit, the conducting conduit forms a spiral, the switch includes a gap between the antenna and the diode, and a conductive material on an antenna-facing side of the membrane, and the pressure switch further comprises:

an adhesive layer adapted to adhere the pressure switch adjacent the tissue site, wherein the antenna is disposed between the adhesive layer and the membrane; and a padding layer disposed between the adhesive layer and the antenna.

14. A pressure switch for monitoring a pressure exerted on a tissue site and adapted for placement adjacent the tissue site and to be responsive to a force applied at the tissue site, the pressure switch comprising:

an antenna operable to receive a first radio frequency signal and propagate a second radio frequency signal in response to the first radio frequency signal;

a diode disposed adjacent the antenna and electrically connected to the antenna to rectify the second radio frequency signal;

a switch electrically connected to the antenna and the diode for completing a circuit when closed; and a membrane covering the antenna and the diode, the membrane movable from an unpressed position to a pressed position when the force is exerted on the membrane to close the switch;

whereby the antenna propagates the second radio frequency signal when the membrane is in the pressed position.

15. The pressure switch apparatus of claim 14 further comprising:

a tactile feedback device operable to output a tactile alert to a patient when the second radio frequency signal is received;

wherein the tactile feedback device is adjacent the pressure switch.

16. The pressure switch of claim 15, wherein the tactile feedback device is coupled to the pressure switch.

17. The pressure switch of claim 15, wherein the tactile feedback device and the pressure switch are located in an off-loading boot.

18. The pressure switch of claim 15, wherein the tactile alert is vibration.

19. The pressure switch of claim 15, wherein the tactile alert is electrical stimulation.

* * * * *